(12) United States Patent
Crivello (10) Patent No.: US 9,822,204 B2
(45) Date of Patent: Nov. 21, 2017

(54) VINYL ETHER FUNCTIONAL OLIGOMERS AND METHODS FOR MAKING AND USING SAME

(75) Inventor: James V. Crivello, Clifton Park, NY (US)

(73) Assignee: RENSSELAER POLYTECHNIC INSTITUTE, Troy, NY (US)

( * ) Notice: Subject to any disclaimer, the term of this patent is extended or adjusted under 35 U.S.C. 154(b) by 916 days.

(21) Appl. No.: 13/825,200

(22) PCT Filed: Sep. 29, 2011

(86) PCT No.: PCT/US2011/053865
§ 371 (c)(1),
(2), (4) Date: Mar. 20, 2013

(87) PCT Pub. No.: WO2012/050951
PCT Pub. Date: Apr. 19, 2012

(65) Prior Publication Data
US 2013/0184371 A1    Jul. 18, 2013

Related U.S. Application Data

(60) Provisional application No. 61/404,235, filed on Sep. 29, 2010.

(51) Int. Cl.
C08F 216/12    (2006.01)
B33Y 70/00    (2015.01)
C08F 222/14    (2006.01)
C07C 69/734    (2006.01)

(52) U.S. Cl.
CPC .......... *C08F 222/14* (2013.01); *C07C 69/734* (2013.01); *C08F 216/125* (2013.01); *B33Y 70/00* (2014.12); *C07C 2601/14* (2017.05)

(58) Field of Classification Search
CPC ............... C08F 222/14; C08F 216/125; C07C 2101/14; C07C 69/734
See application file for complete search history.

(56) References Cited

U.S. PATENT DOCUMENTS 6,767,933 B2 *   7/2004   Garnett ................. C08F 222/06
                                                        427/500

FOREIGN PATENT DOCUMENTS

WO          02-20677 A1      3/2002

OTHER PUBLICATIONS

Crivello et al., "Photoinitiated Alternating Copolymerization of Dialkyl Maleates and Fumarates with Vinyl Ethers", J. Poly. Sci: Part A: Polymer Chemistry, vol. 48 (p. 4726-4736), Sep. 7, 2010.*

(Continued)

*Primary Examiner* — Michael Pepitone
*Assistant Examiner* — Jessica Roswell
(74) *Attorney, Agent, or Firm* — Heslin Rothenberg Farley & Mesiti P.C.; Nathan Brain Davis (57) ABSTRACT

The present invention includes vinyl ether functional oligomers and methods for their preparation, the method including alternating free radical copolymerization of a dialkyl maleate or dialkyl fumarate monomer with a multi-functional vinyl ether monomer in the presence of a solvent with a high chain transfer constant. Also within the scope of the invention are uses for the vinyl ether functional oligomers compositions of this invention, including radiation curable coatings, adhesives, printing inks and composites.

20 Claims, 7 Drawing Sheets

(56) References Cited

OTHER PUBLICATIONS

Tsarik, L. Ya, et al; "Copolymerization of Divinyl Monomers with Maleic and Fumaric Acid Derivatives," J. Polym. Sci.: Part A: Polym. Chem. 1998, vol. 36, 371-378.
Katogi, Shigeki, et al; "Photopolymerization of dialkyl fumarates with electron donor monomers," Polymer 1998, vol. 39, 2709-2714.
Wei, Huanyu, et al; "Characterization and Photopolymerization of Divinyl Fumarates," Macromolecules 2007, vol. 40, 6172-6180.
International Search Report for PCT/US2011/053865 dated Apr. 24, 2012.

* cited by examiner

VINYL ETHER FUNCTIONAL OLIGOMERS AND METHODS FOR MAKING AND USING SAME

CROSS REFERENCE TO RELATED APPLICATIONS

This application is a U.S. National Phase filing under 35 U.S.C. §371 of International Application PCT/US2011/053865, filed Sep. 29, 2011, and published as WO 2012/050951 on Apr. 19, 2012. PCT/US2011/053865 claimed benefit of priority to U.S. Provisional Application No. 61/404,235, filed Sep. 29, 2010. The entire contents of each of the prior applications are hereby incorporated herein by reference.

TECHNICAL FIELD

The present invention generally relates to vinyl ether functional oligomers and their use in forming polymers.

BACKGROUND INFORMATION

Oligomers bearing polymerizable functional groups are very important in many commercial applications including coatings, adhesives and composites. These reactive oligomers provide critical film-forming, adhesive, flexural and impact modification that are essential for success in those applications. Vinyl ether polymers and oligomers constitute a classical group of starting materials for the production of adhesives and coatings. They are primarily used in combination with other raw materials or in making pressure-sensitive adhesives, usually by blending with acrylic dispersions. In the field of surface coatings, polyvinyl ethers are formulated together with cellulose nitrate, chlorinated binders, and styrene copolymers for coating metal foil, plastics, film, paper, and other flexible substrates, and for antifouling paints. Oligomers bearing polymerizable functional groups are especially important in the fields of UV and electron-beam curing where polymerization takes place at time scales of the order of seconds. In such cases, oligomers bearing polymerizable functional groups not only provide film-forming characteristics, but also allow uniform application, control flow, and limit penetration into porous substrates. Especially valuable is the use of these oligomers to control shrinkage and enhance the efficiency of crosslinking during photopolymerization.

SUMMARY OF THE INVENTION

The vinyl ether functional oligomer compositions of this invention have many applications including radiation curable coatings, adhesives, printing inks and composites. In addition, these oligomers have additional potential uses in imaging applications such as photoresists and for 3-dimensional imaging techniques such as ink jet printing and stereolithography.

In one aspect, the invention includes an oligomer comprising repeating units of formula I wherein
$R^1$ is a non-olefinic and non-acetylenic ($C_1$-$C_{10}$)hydrocarbon;
$R^2$ is a non-olefinic and non-acetylenic ($C_1$-$C_{10}$)hydrocarbon; and
$R^3$ is a non-olefinic and non-acetylenic ($C_1$-$C_{24}$)hydrocarbon, wherein one or more alkylene ($CH_2$) optionally may be replaced by —O—, —S—, or $SO_2$ in each instance.

In a second aspect, the invention includes an oligomer obtainable by the process comprising preparing a mixture of
a. at least one monomer of formula A wherein
$R^1$ is a non-olefinic and non-acetylenic ($C_1$-$C_{10}$)hydrocarbon;
$R^2$ is a non-olefinic and non-acetylenic ($C_1$-$C_{10}$)hydrocarbon; and
b. at least one monomer of formula B wherein $R^3$ is a non-olefinic and non-acetylenic ($C_1$-$C_{24}$) hydrocarbon group, wherein one or more alkylene ($CH_2$) optionally may be replaced by —O—, —S—, or $SO_2$ in each instance; in the presence of a free radical initiator in a solvent with a high radical chain transfer constant,
wherein the molar ratio of the monomer of formula A to the monomer of formula B is approximately 1:1.

In a third aspect, the invention includes a composition comprising:
a. A monomer of formula A b. A monomer of formula B and c. A solvent with a high radical chain transfer constant;
wherein
$R^1$ is a non-olefinic and non-acetylenic ($C_1$-$C_{10}$)hydrocarbon;
$R^2$ is a non-olefinic and non-acetylenic ($C_1$-$C_{10}$)hydrocarbon;
$R^3$ is a non-olefinic and non-acetylenic ($C_1$-$C_{24}$)hydrocarbon, wherein one or more alkylene ($CH_2$) optionally may be replaced by —O—, —S—, or $SO_2$ in each instance; and wherein the molar ratio of the monomer of formula A to the monomer of formula B is approximately 1:1.

In a fourth aspect, the invention includes a method for preparing an oligomer, said method comprising preparing a mixture of
a. at least one monomer of formula A wherein
$R^1$ is a non-olefinic and non-acetylenic ($C_1$-$C_{10}$)hydrocarbon;
$R^2$ is a non-olefinic and non-acetylenic ($C_1$-$C_{10}$)hydrocarbon; and
b. at least one monomer of formula B wherein $R^3$ is a non-olefinic and non-acetylenic ($C_1$-$C_{24}$) hydrocarbon, wherein one or more alkylene ($CH_2$) optionally may be replaced by —O—, —S—, or $SO_2$ in each instance;
in the presence of a free radical initiator in a solvent with a high radical chain transfer constant;
wherein the ratio of the monomer of formula A to the monomer of formula B is approximately 1:1.

In a fifth aspect, the invention includes a kit for preparing oligomers comprising:
a. a mixture comprising
 i. at least one monomer of formula A wherein
$R^1$ is a non-olefinic and non-acetylenic ($C_1$-$C_{10}$)hydrocarbon;
$R^2$ is a non-olefinic and non-acetylenic ($C_1$-$C_{10}$)hydrocarbon;
 ii. at least one monomer of formula B wherein $R^3$ is a non-olefinic and non-acetylenic ($C_1$-$C_{24}$) hydrocarbon, wherein one or more alkylene ($CH_2$) optionally may be replaced by —O—, —S—, or $SO_2$ in each instance; in a solvent with a high radical chain transfer constant;
wherein the ratio of the monomer of formula A to the monomer of formula B is approximately 1:1; and
b. a second component comprising a free radical initiator, optionally in a solvent with a high radical chain transfer constant.

In a sixth aspect, the invention includes a process for forming a polymer comprising:
a. Combining at least one oligomer of the invention with a cationic photoinitiator; and
b. Exposing the resulting combination to actinic irradiation.

In a seventh aspect, the invention includes a process for forming a polymer comprising:
a. Combining at least one oligomer of the invention, at least one free radically polymerizable vinyl monomer and a free radical photoinitiator; and
b. Exposing the resulting combination to actinic irradiation.

These and other objects, features and advantages of this invention will become apparent from the following detailed description of the various aspects of the invention taken in conjunction with the accompanying examples.

Photoinitiated free radical alternating copolymerizations of dialkylmaleates or dialkylfumarates together with multifunctional vinyl ethers occur only when both types of monomers are present. As a result, copolymers are formed. Neither the maleate or fumarate monomer, nor the vinyl ether monomer, undergoes free radical polymerization by itself (i.e. homopolymerization). When the photocopolymerizations of these two classes of monomers are carried out in a stoichiometric 2:1 ratio with a divinyl ether (as depicted in equation 1), a crosslinked network copolymer is formed. The photopolymerizations of dialkyl maleates and dialkyl fumarates with multifunctional vinyl ethers are fast and efficient, and the network copolymers that are obtained are transparent and colorless. Depending on the respective three R groups in the monomers, copolymers that are obtained range from stiff, brittle and glass-like to highly flexible.

(1)

cis and trans

In this invention, a modification of the stoichiometry shown in equation 1 leads to the production of reactive oligomers bearing vinyl ether groups. The average functionality of a mutually reactive multicomponent system s determined by the functionality of the minority component present in the mixture (G. Odian, Principles of Polymerization, 4th Ed., Wiley-Interscience, New York, 2005, pp. 105-108.). Thus, as shown below in equation 2, a 1:1 equimolar mixture of a dialkyl maleate- or fumarate-based monomer (difunctional, formula A) with a divinyl ether (tetrafunctional, formula B) has an average functionality of 2. As depicted in equation 2, a linear or branched alternating copolymer can be formed bearing pendant vinyl ether groups. The polymer does not crosslink easily and is, therefore, soluble in common solvents or monomers.

Reactive oligomers such as those described in equation 2 bearing pendant vinyl ether groups are of considerable interest for a variety of potential uses. For example, these oligomers would be particularly advantageous for use in UV curing applications. As noted in equation 2, the reactive oligomer could be combined with the same or a different dialkyl maleate- or fumarate-based monomer and then photopolymerized using a free radical photoinitiator. In addition to dialkyl maleates and fumarates, other free radically polymerizable vinyl monomers can be used. For example, the oligomers of this invention can be photopolymerized with mono- or multifunctional acrylates and methacrylates.

Alternatively, the same reactive vinyl ether functional oligomer could be directly mixed with a cationic photoinitiator and then UV irradiated to give a crosslinked network. In this case, crosslinking occurs by direct homopolymerization of the vinyl ether groups located along the backbone of the oligomer. A further modification consists of adding low molecular weight mono-, di- or multifunctional vinyl ethers to the oligomer and then performing the cationic photopolymerization. Since vinyl ether monomers are extraordinarily reactive under cationic polymerization conditions, these two strategies would appear to give rise to very rapidly curing compositions well suited to high volume, high speed applications such as printing inks and coatings. A further expectation from the use of these oligomers in either free radical or cationic photopolymerization is the substantial reduction in shrinkage that occurs when they are used. Essentially, a great deal of the overall shrinkage is removed by first making the oligomers and then subjecting them to a further crosslinking photopolymerization.

A large number of attempts were made to carry out the copolymerization of 1:1 mixtures of various dialkyl maleates or dialkyl fumarates with difunctional vinyl ethers in the presence of such free radical initiators as benzoyl peroxide and AIBN. Although theory might predict that linear or branched polymers should result, invariably, when these copolymerizations were conducted in the absence of a solvent, gelled (i.e. crosslinked) products were obtained. On the other hand, when the copolymerizations of maleate and fumarate monomers with divinyl ethers were conducted in the presence of a solvent with a high radical chain transfer constant, the polymerization was surprisingly successful.

The methodology depicted in equation 2 is readily applicable to the synthesis of a wide range of vinyl ether functional oligomers. Each of the three R groups shown in this equation can be varied to provide oligomers with a broad array of chemical, mechanical and physical properties on cure. The molecular weight and viscosity of the oligomers can be controlled by the concentration of the free radical initiator employed in the synthesis. Typically, the oligomers described here are colorless or very pale yellow colored viscous fluids. The oligomers can be used directly as prepared in various applications or further diluted with various maleate, fumarate, acrylate, methacrylate, styrenic or vinyl ether monomers to provide photo—, electron-beam or thermally curable mixtures.

It is also worth noting that multifunctional vinyl ethers are rather high priced materials. For this reason, multifunctional vinyl ethers cannot compete with acrylates in most UV cure applications. On the other hand, dialkyl maleates or dialkyl fumarates are very inexpensive materials. The strategy of copolymerization of multifunctional vinyl ethers with maleates and fumarates is attractive since it results in an overall systems cost reduction together with an upgrade in chemical, mechanical and physical properties.

DETAILED DESCRIPTION OF THE INVENTION

Definitions

Throughout this specification and in all independent claims the terms and substituents retain their definitions.

Hydrocarbon refers to any substituent comprised of hydrogen and carbon as the only elemental constituents. Unless otherwise specified, hydrocarbon includes alkyl, polycycloalkyl, alkenyl, alkynyl, aryl and combinations thereof. Examples include benzyl, phenethyl, cyclohexylmethyl, dimethylcyclohexane and naphthylethyl. Although the definition of hydrocarbon includes alkenyl and alkynyl, those hydrocarbons that contain double and triple bonds are excluded from the present invention. $C_1$ to $C_{10}$ hydrocarbon [or $(C_1-C_{10})$hydrocarbon] includes any hydrocarbon containing 1, 2, 3, 4, 5, 6, 7, 8, 9 or 10 carbon atoms, along with their corresponding hydrogen atoms. Similarly, $C_1$ to $C_{24}$ hydrocarbon includes any hydrocarbon containing 1, 2, 3, 4, 5, 6, 7, 8, 9, 10, 11, 12, 13, 14, 15, 16, 17, 18, 19, 20, 21, 22, 23 or 24 carbon atoms, along with their corresponding hydrogen atoms.

Unless otherwise specified, alkyl is intended to include linear, branched, or cyclic hydrocarbon structures and combinations thereof. A combination would be, for example, dimethylcyclohexane. $C_1$ to $C_8$ alkyl [or $(C_1-C_8)$alkyl] refers to alkyl groups containing 1, 2, 3, 4, 5, 6, 7 or 8 carbon atoms. Examples of $(C_1-C_8)$alkyl groups include methyl, ethyl, propyl, isopropyl, butyl, s- and t-butyl and the like. Cycloalkyl is a subset of alkyl and includes cyclic hydrocarbon groups containing 3 to 8 carbon atoms. Examples of cycloalkyl groups include c-propyl, c-butyl, c-pentyl, c-hexyl, norbornyl and the like.

Oxaalkyl refers to alkyl residues in which one or more carbons (and their associated hydrogens) have been replaced by oxygen. Non-limiting examples include methoxypropoxy, ethoxyethane and diethoxymethane. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups.

According to IUPAC, a polymer is "a molecule of high relative molecular mass, the structure of which essentially comprises the multiple repetition of units derived, actually or conceptually, from molecules of low relative molecular mass." Also according to IUPAC, an oligomer is "a molecule of intermediate relative molecular mass, the structure of which essentially comprises a small plurality of units derived, actually or conceptually, from molecules of lower relative molecular mass." For the purpose of the present invention we define the cutoff between oligomer and polymer to occur at 100 repeating units of A plus B in total. Thus a molecule that comprises 50 repeating units A and 50 repeating units B (or fewer) is an oligomer; a molecule that comprises 51 repeating units A and 51 repeating units B is a polymer.

Examples of monofunctional or multifunctional acrylates and monofunctional or multifunctional methacrylates that can be free radically polymerized include: ethylene glycol diacrylate, allyl acrylate, hydroxyethylacrylate, 1,4-butanediol diacrylate, isobornyl acrylate, n-butyl acrylate, lauryl acrylate, trimethylolpropane triacrylate, pentaerythritol tetraacrylate, trimethylolethane triacrylate, bisphenol-A-diacrylate, diethylene glycol diacrylate, triethylene glycol diacrylate, dipentaerythritol hexaacrylate, 1,4-cyclohexanedimethanol diacrylate, ethylene glycol dimethacrylate, 1,6-hexanediol dimethacrylate, hydroxyethylmethacrylate and polyurethane diacrylate oligomers. Among other possible free radically polymerizable monomers are: dimethyl maleate, dimethyl fumarate, diethyl maleate, di-n-butyl maleate, di-n-octylmaleate, diethylfumarate, dimethylitaconate.

In one aspect, the invention includes an oligomer comprising repeating units of formula I Structure I In some embodiments of the invention, the oligomer further comprises a plurality of units of formula II

Structure II

It is important to note that the repeating units may be in any order, and it is not necessary for more than one unit of formula I to be adjacent to another, although that may be the case in some instances. Although the oligomer may contain units such as structure II, on average the main units are those of structure I.

In some embodiments of the invention, $R^1$ is a non-olefinic and non-acetylenic $(C_1$-$C_{10})$hydrocarbon. In some embodiments, $R^1$ is methyl. In other embodiments, $R^1$ is ethyl. In still other embodiments, $R^1$ is propyl. In yet other embodiments, $R^1$ is butyl. In some embodiments, $R^1$ is 2-ethylhexyl.

In some embodiments of the invention, $R^2$ is a non-olefinic and non-acetylenic $(C_1$-$C_{10})$hydrocarbon. In some embodiments, $R^2$ is methyl. In other embodiments, $R^2$ is ethyl. In still other embodiments, $R^2$ is propyl. In yet other embodiments, $R^2$ is butyl. In some embodiments, $R^2$ is 2-ethylhexyl.

In some embodiments of the invention, $R^3$ is a non-olefinic and non-acetylenic $(C_1$-$C_{24})$hydrocarbon. In some embodiments of the invention, one or more alkylene ($CH_2$) may be replaced by —O—. In other embodiments of the invention, one or more alkylene ($CH_2$) may be replaced by —S—. In still other embodiments of the invention, one or more alkylene ($CH_2$) may be replaced by $SO_2$. It is important to note that each replaced alkylene ($CH_2$) may be replaced by any one of —O—, —S—, or $SO_2$. The person of skill in the art will be aware of those replacements that are not chemically stable; residues that are chemically stable are preferred. In some embodiments of the invention, $R^3$ is one of the two formulae below:

In some embodiments, X is a direct bond. In other embodiments, X is $C(CH_3)_2$ or $CH_2$. In still other embodiments, X is O. In yet other embodiments, X is S or $SO_2$. In other embodiments of the invention, $R^3$ is selected from $(C_1$-$C_8)$ alkyl and $(C_1$-$C_8)$oxaalkyl. Some non-limiting examples of $R^3$ include In other embodiments, the invention relates to an oligomer obtainable by the process comprising reacting at least one monomer of formula A with at least one monomer of formula B in the presence of a free radical initiator in a solvent with a high radical chain transfer constant. In these embodiments, the ratio of the monomer of formula A to the monomer of formula B is approximately 1:1.

The free radical initiator of the invention preferably has a convenient half life and undergoes fragmentation by thermolysis to give pH neutral products that do not interfere with the subsequent radical or cationic polymerizations. Additionally, these fragments react further with the vinyl ether groups present in the oligomeric product. In some embodiments of the invention, the free radical initiator is an azo inhibitor. In other embodiments, the free radical initiator is a peroxy or hydroperoxy initiator. In still other embodiments, the free radical initiator is a peroxyalkyl initiator. In some embodiments, the free radical initiator is 2,2'-Azobisisobutyronitrile. The half-life of 2,2'-Azobisisobutyronitrile (AIBN) is 80 min at 80° C. Other suitable free radical initiators include benzoyl peroxide, dicumylperoxide, t-butyl hydroperoxide, cumene hydroperoxide, acetyl peroxide, lauroyl peroxide, t-butyl perbenzoate, t-butyl peroxypivalate, 2,2'-azobis-2-ethylpropionitrile, 4,4'-az0-bis(cyanopentanol) (a comprehensive list of applicable free radicals can be found in Polymer Handbook, $4^{th}$ Ed. Vol. 1, by J. Brandrup, E. H. Immergut and E. A. Grulke (editors) Wiley-Interscience, New York, 1999, p. II/1.

The chain transfer constant of the solvent may range from 10-60,000. Suitable solvents with known high free radical chain transfer constants are for example: p-dioxane; tetrahydrofuran, 1,3-dioxolane, 1,2-dimethoxyethane and diethyleneglycol dimethyl ether. A comprehensive list of applicable free radicals constants for various solvents and additives can be found in Polymer Handbook, $4^{th}$ Ed. Vol. 1, by J. Brandrup, E. H. Immergut and E. A. Grulke (editors) Wiley-Interscience, New York, 1999, p. II/111. The chain constants are a function of the specific solvent, the monomer(s) and the temperature at which the polymerization is carried out. Solvents with high transfer constants would be those with values above 1000.

In addition to having a high free radical chain transfer constant, the solvent should have a relatively low boiling point so that it may be readily removed from the oligomer by vacuum stripping and so that the copolymerization can be carried out in a convenient time period (less than 10 hours) under refluxing conditions. For instance, 1,2-dimethoxyethane is an excellent solvent for the two monomers and has a boiling point of 85°, which allows the copolymerization to be carried out in approximately 3-5 hours under refluxing conditions. In some embodiments of the invention, the solvent with a high radical chain transfer constant is 1,2- dimethoxyethane. In other embodiments, the solvent is 1,4-dioxane. In still other embodiments, the solvent is 1,3-dioxolane. In yet other embodiments, the solvent is tetrahydrofuran. In other embodiments, the solvent is diethylene glycol dimethyl ether. In some embodiments, the solvent is di(n-butyl)ether.

In some embodiments, the invention relates to a composition comprising a monomer of formula A:

$$R^2O_2C-CH=CH-CO_2R^1 \qquad A;$$

a monomer of formula B:

and a solvent with a high radical chain transfer constant. In these embodiments, the ratio of the monomer of formula A to the monomer of formula B may be approximately 1:1. These compositions are useful in that they can be packaged and transported readily, and subsequently the oligomers described herein can be made simply by mixing these compositions with a suitable catalyst at an appropriate temperature.

In some embodiments, the invention relates to a process for preparing an oligomer comprising reacting a monomer of formula A with a monomer of formula B in the presence of a free radical initiator in a solvent with a high radical chain transfer constant. In these embodiments, the ratio of the monomer of formula A to the monomer of formula B may be approximately 1:1.

In some embodiments, the invention relates to a kit for preparing oligomers comprising two components. The first component comprises a mixture of a monomer of formula A with a monomer of formula B in a solvent with a high radical chain transfer constant. In these embodiments, the ratio of the monomer of formula A to the monomer of formula B approximately 1:1. The second component comprises a free radical initiator, optionally in a solvent with a high radical chain transfer constant.

In some embodiments, the invention relates to process for forming a polymer. In these embodiments, the process first comprises combining at least one oligomer as described above with a cationic photoinitiator. In some embodiments, the cationic photoinitiator is a diaryliodonium salt. In other embodiments, the cationic photoinitiator is a triarylsulfonium salt. In some embodiments, the cationic photoinitiator is (4-n-octyloxyphenyl)phenyliodonium hexafluoroantimonate (IOC-8 $SbF_6^-$).

In some embodiments of the invention, additional amounts of the monomer of formula B may be added to the oligomer and the cationic photoinitiator. In some embodiments, this additional monomer of formula B is added in a molar amount equivalent to the vinyl ether groups present in the oligomer.

The resulting combination is then exposed to actinic irradiation. For instance, ultraviolet irradiation may be employed. The use of aromatic onium salts such as diaryliodonium and triarylsulfonium salts as photoacid generators in photolithography and as photoinitiators for cationic photopolymerizations is well documented. Most onium salts are intrinsically photoactive in the short and middle wavelength region of the UV spectrum and hence, no photosensitizer is required. However, photosensitizers are commonly added when radiation outside that range is employed. Polynuclear aromatic hydrocarbons such as anthracene, pyrene, and perylene have the requisite long wavelength absorption characteristics and also undergo efficient photoinduced electron-transfer photosensitization with onium salt photoinitiators. Other photosensitizers for diaryliodonium and triarylsulfonium salts are well-known in the art and can be employed in the compositions herein.

In other embodiments, the invention relates to another process for forming a polymer. In these embodiments, the process first comprises combining at least one oligomer as described above with at least one free radically polymerizable monomer and a free radical photoinitiator.

In some embodiments of the invention, the free radically polymerizable monomer is a monomer of formula A. In other embodiments; the free radically polymerizable vinyl monomer is styrene. In other embodiments, the free radically polymerizable monomer is a monofunctional or multifunctional acrylate. In still other embodiments, the free radically polymerizable monomer is a monofunctional or multifunctional methacrylate. In some embodiments, the free radically polymerizable monomer is a monomer of formula A added at a molar equivalent to that of the oligomer (that is, a molar equivalent amount of A to the amount of vinyl ether groups present in the oligomer).

In some embodiments of the invention, the free radical photoinitiator is selected from 2-hydroxy-2,2-dimethoxyacetophenone, 1-hydroxycyclohexylphenyl ketone, 2,2-dimethoxy-2-phenylacetophenone, bis(2,4,6-trimethylbenzoyl)-phenylphosphine oxide, 2,4,6-trimethylbenzoyldiphenylphosphine oxide, n-butylbenzoin ether, mixtures of benzophenone and triethanol amine and 4,4'-bis(N,N-dimethylamino)benzophenone. Other examples of appropriate free radical photoinitiators can be found in J. V. Crivello and K. K. Dietliker, "Photoinitiators for Cationic Polymerization" Chemistry and Technology of UV & EB Formulation for Coatings, Inks & Paints, 1991, E.M. Books, Ltd., London, Volume III, P. K. T. Oldring, Editor, p. 327.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Similarly, when the compounds described herein contain olefinic double bonds or other centers of geometric asymmetry, and unless specified otherwise, it is intended that the compounds include both E and Z geometric isomers. For example, unless otherwise specified, a drawn structure could represent either diethyl maleate or diethyl fumarate. Likewise, all tautomeric forms are also intended to be included.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

Abbreviations
AIBN=2,2'-Azobisisobutyronitrile
BDDVE=1,4-butanediol divinyl ether
CHDDVE=1,4-cyclohexanedimethanol divinyl ether
DBM=dibutyl maleate DEM=diethyl maleate
DMM=dimethyl maleate
DVE-3=triethyleneglycol divinyl ether
IOC-8 SbF$_6^-$=(4-n-octyloxyphenyl)phenyliodonium hexafluoroantimonate
OP=optical pyrometry
TMPTVE=trimethylolpropane trivinyl ether
UV=Ultraviolet

EXAMPLES

Explained herein are examples of embodiments of the invention. The invention may, however, be embodied in many different forms and should not be construed as being limited to the exemplary embodiments set forth herein; rather, these embodiments are provided so that this disclosure will be thorough and complete, and will convey the concept of the invention to those skilled in the art.

Figure 1:
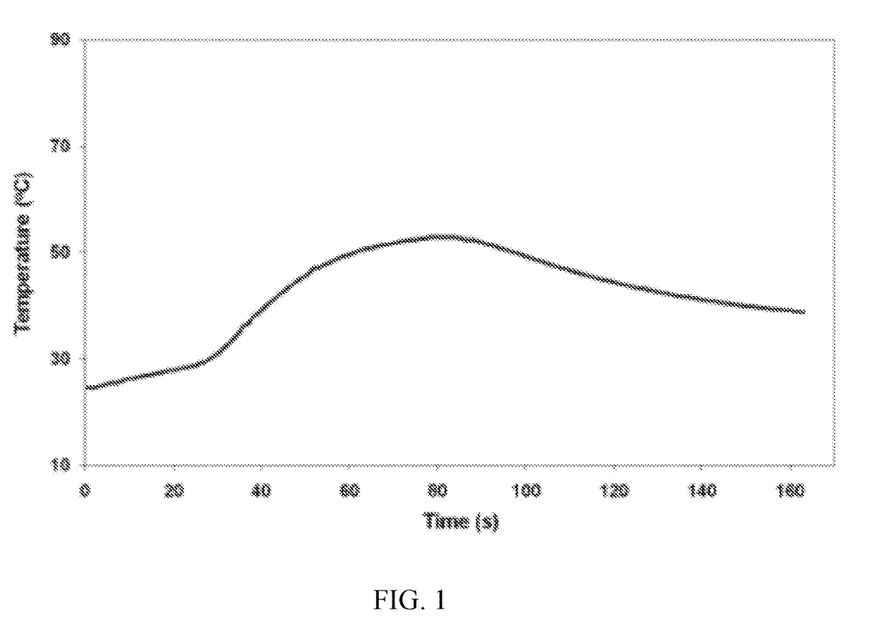
FIG. 1 is an OP study of the photopolymerization of diethylmaleate/1,4-butanediol divinyl ether (DEM-BD-DVE) reactive oligomer with 2% by weight of (4-octyloxyphenyl)-phenyliodonium hexafluoroantimonate (IOC-8SbF$^{6-}$) as the photoinitiator (light intensity 2700 mJ/cm$^2$ min.), in accordance with the present invention.

FIG. 1 is an OP study of the photopolymerization of DEM-BDDVE reactive oligomer with 2% by weight of IOC-8 SbF6– as the photoinitiator (light intensity 2700 mJ/cm2 min.). A description of the Optical Pyrometry apparatus and methods for its use are to be found in: B. Falk, S. M Vallinas and J. V. Crivello "Monitoring Photopolymerization Reactions Using Optical Pyrometry" J. Polym. Sci., Part A: Polym. Chem. Ed., 41(4), 579-596 (2003).

Figure 2:
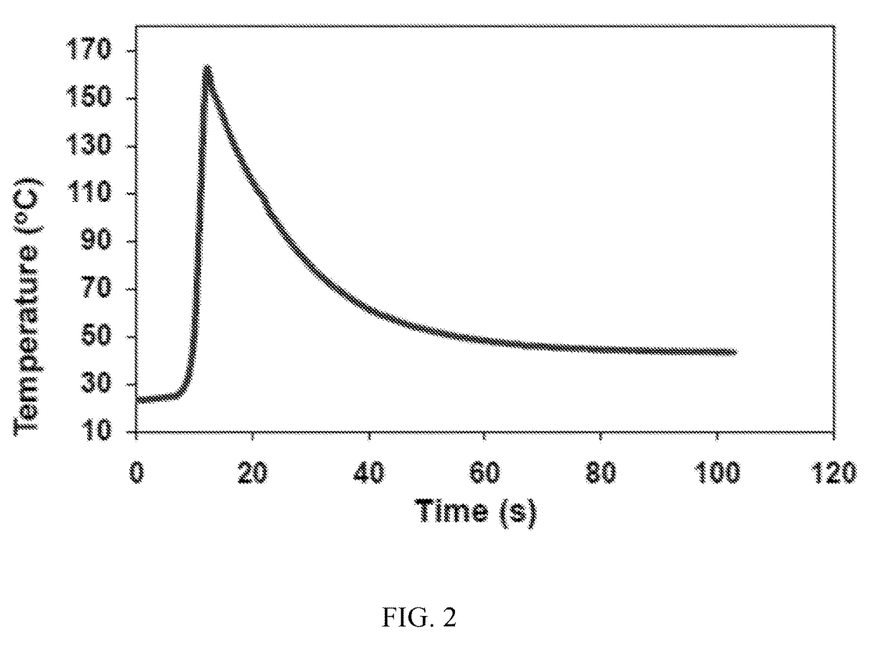
FIG. 2 shows cationic photopolymerization of DEM-BDDVE reactive oligomer with 50% by weight of BDDVE using 2% by weight of IOC$^{-8}$ SbF$^{6-}$ as the photoinitiator (light intensity 2700 mJ/cm$^2$ min.), in accordance with the present invention.

FIG. 2 shows photopolymerization of DEM-BDDVE reactive oligomer with 50% by weight of BDDVE using 2% by weight of IOC-8 SbF6– as the photoinitiator (light intensity 2700 mJ/cm2 min.).

Figure 3:
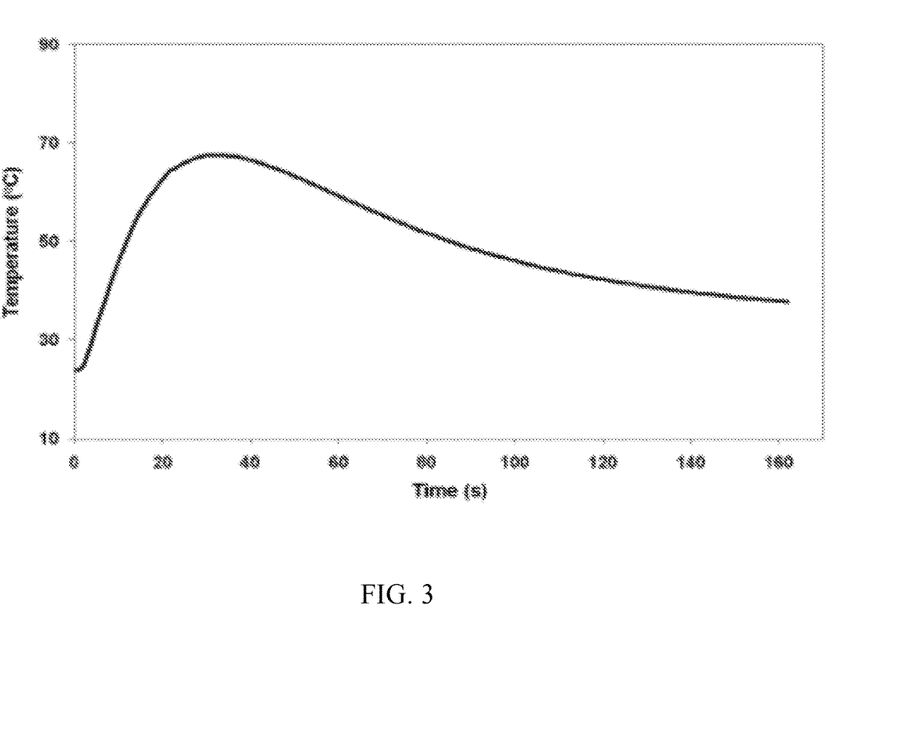
FIG. 3 presents free radical photopolymerization of DEM-BDDVE reactive oligomer with one equivalent of DEM using 2% by weight of Darocure-1173 as the photoinitiator (light intensity 2700 mJ/cm$^2$ min.), in accordance with the present invention.

FIG. 3 presents photopolymerization of DEM-BDDVE reactive oligomer with one equivalent of DEM using 2% by weight of Darocure-1173 as the photoinitiator (light intensity 2700 mJ/cm2 min.).

Figure 4:
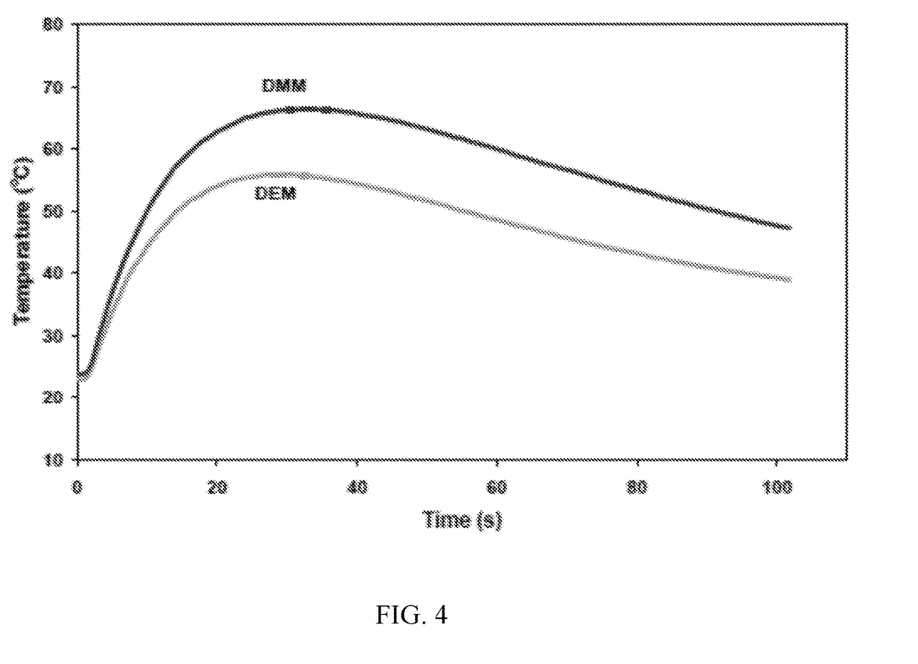
FIG. 4 depicts the free radical photopolymerization of the vinyl ether functional CMDVE-DEM oligomer with equivalent amounts of either DEM or DMM using 3% Irgacure 184 (1-hydroxycyclohexylphenyl ketone) as the photoinitiator (light intensity 2700 mJ/cm$^2$ min.), in accordance with the present invention.

FIG. 4 depicts the free radical photopolymerization of the vinyl ether functional CMDVE-DEM oligomer with equivalent amounts of either DEM or DMM using 3% Irgacure 184 (1-hydroxycyclohexylphenyl ketone) as the photoinitiator (light intensity 2700 mJ/cm2 min.).

Figure 5:
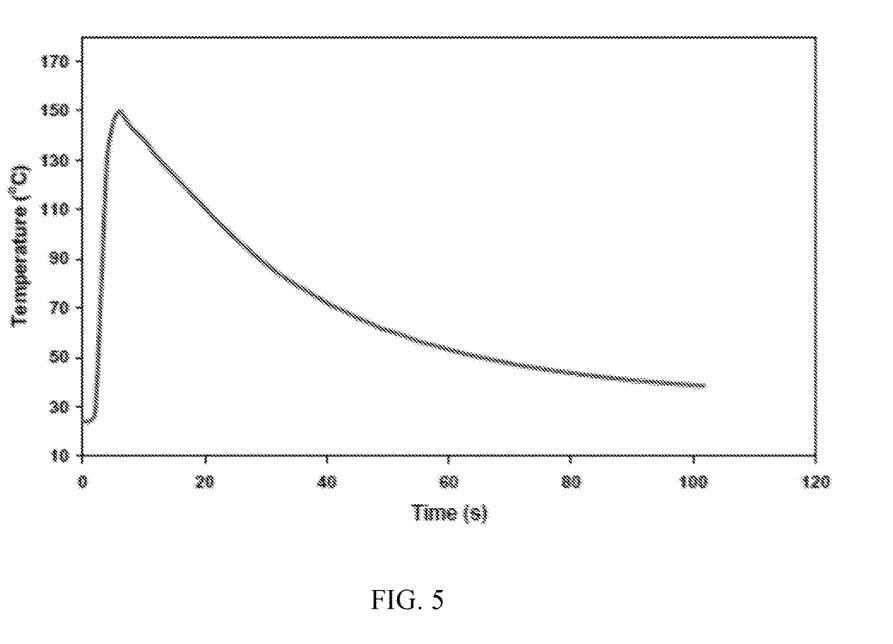
FIG. 5 shows the free radical photopolymerization of DEM-DVE-3 oligomer with 50% 1,6-hexanediol diacrylate with 3% Darocure-1173 (light intensity 2700 mJ/cm$^2$ min.), in accordance with the present invention.

FIG. 5 shows Photopolymerization of DEM-DVE-3 oligomer with 50% 1,6-hexanediol diacrylate with 3% Darocure-1173 (light intensity 2700 mJ/cm2 min.).

Figure 6:
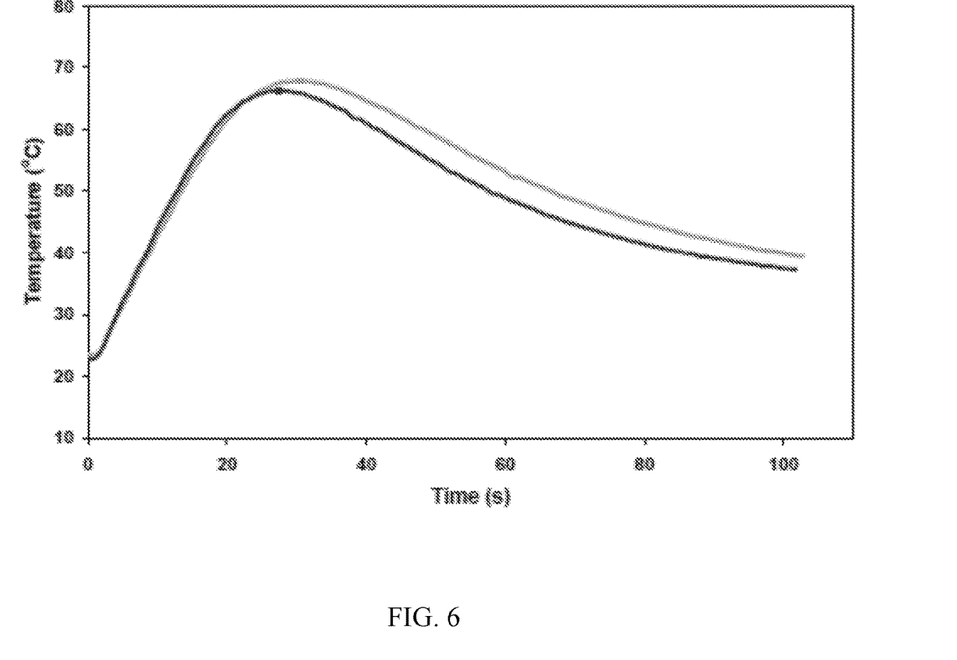
FIG. 6 shows an OP study of the photopolymerization of a 1:1 molar mixture of DBM-DVE-3 oligomer with DMM with 3% by weight of Darocure-1173 (light intensity 2700 mJ/cm$^2$ min.), in accordance with the present invention. Duplicate runs are shown.

FIG. 6 shows an OP study of the photopolymerization of a 1:1 molar mixture of DBM-DVE-3 oligomer with DMM with 3% by weight of Darocure-1173 (light intensity 2700 mJ/cm2 min.). Duplicate runs are shown.

Figure 7:
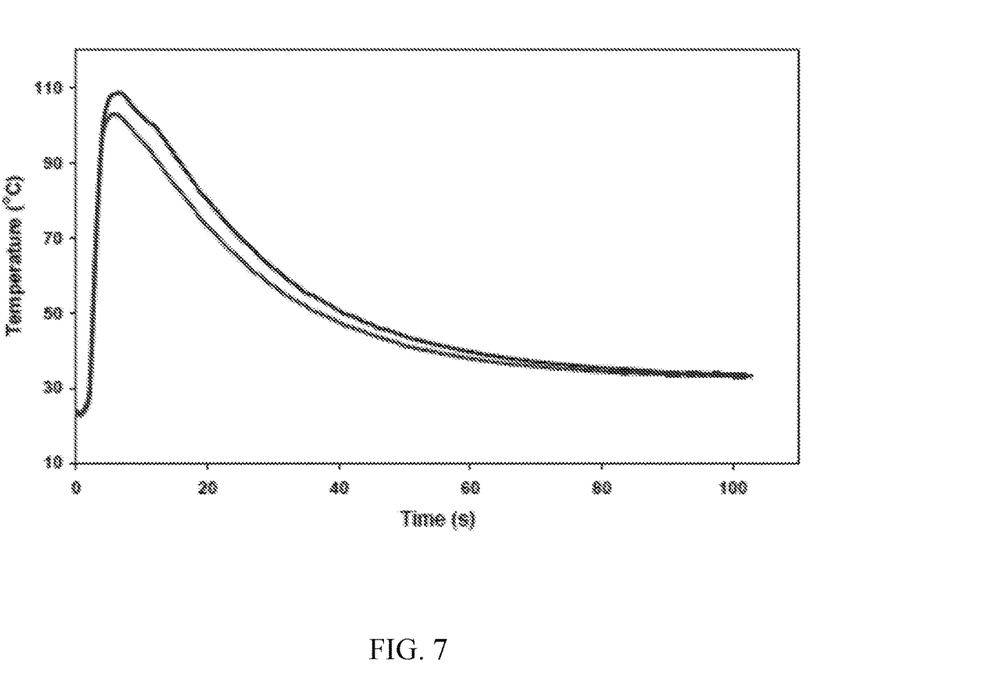
FIG. 7 shows an OP study of the photopolymerization of a 2:1 wt/wt mixture of DEF-DVE-3 oligomer with 1,6-hexanediol diacrylate with 3% by weight of Darocure-1173 (light intensity 2700 mJ/cm$^2$ min.), in accordance with the present invention. Duplicate runs are shown.

FIG. 7 shows an OP study of the photopolymerization of a 2:1 wt/wt mixture of DEF-DVE-3 oligomer with 1,6-hexanediol diacrylate with 3% by weight of Darocure-1173 (light intensity 2700 mJ/cm2 min.). Duplicate runs are shown.

Materials

The free radical photoinitiators Irgacure 184, and Darocure 1173 were provided as samples by the Ciba Specialty Chemicals, Inc., Basel, Switzerland. All the alkyl maleate and fumarate esters, 1,6-hexanediol diacrylate and 2,2'-azobisisobutyronitrile (AIBN) were used as purchased from the Aldrich Chemical Co., Milwaukee, Wis. and from TCI America, Portland, Oreg. A sample of triethylene glycol divinyl ether (DVE-3) was kindly provided by International Specialty Products, Wayne, N.J. Similarly, 1,4-butarediol divinyl ether (BDDVE), 1,4-cyclohexanedimethanol divinyl ether (CHDDVE) and trimethylolpropane trivinyl ether (TMPTVE) were supplied by the BASF Corporation, Ludwigshafen, Germany. The cationic photoinitiator, (4-n-octyloxyphenyl)phenyliodonium hexafluoroantimonate (IOC-8 SbF$_6$–) was prepared as described previously (J. V. Crivello and J. L. Lee, J Polym Sci Part A: Polym Chem 1989, 27, 3951-3968). All other reagents and chemicals were used as purchased from the Aldrich Chemical Co.

Example 1

Preparation of Vinyl Ether Oligomers

DEM-DVE-3 Oligomer: Into a 2-neck 50 ml round bottom flask equipped with a nitrogen inlet, a magnetic stirrer and a reflux condenser were placed 1.72 g (0.01 mol) diethyl maleate, 2.02 g (0.01 mol) triethyleneglycol divinyl ether (DVE-3), 0.019 g (0.5 wt %) AIBN and 10 ml 1,2-dimethoxyethane. The reaction mixture was first flushed with nitrogen and then heated to 80° C. under a nitrogen atmosphere for 3 hours. After cooling, the reaction mixture was stripped of solvent on a rotary evaporator leaving a pale yellow oil (2.76 g, 74% yield). A significant amount of the oligomer was lost during handling. An infrared spectrum recorded on a Nicolet 4700 FT-IR spectrometer showed the presence of a prominent strong bands at 1616 cm-1 and 1734.5 cm-1 due respectively to the vinyl ether carbon-carbon double bonds and the carbonyl bond. At the same time, the band at 1404.8 cm$^{-1}$ assigned to the maleate double bond of DEM was absent. This indicates that the alternating polymerization proceeds efficiently and quantitatively to produce the desired oligomer with the structure shown in equation 2 ($R^1$, $R^2$=ethyl; $R^3$=(—CH$_2$CH$_2$—O—CH$_2$CH$_2$—O—CH$_2$CH$_2$—).

The above reaction was repeated under slightly different reaction conditions.

Into a 2-neck 50 ml round bottom flask equipped with a nitrogen inlet, a magnetic stirrer and a reflux condenser were placed 5.16 g (0.03 mol) diethyl maleate, 6.06 g (0.03 mol) triethyleneglycol divinyl ether (DVE-3), 0.22 g (2.0 wt %) AIBN and 25 ml 1,2-dimethoxyethane. The reaction mixture was first flushed with nitrogen and then heated to 80-85° C. under a nitrogen atmosphere for 5 hours. After cooling, the reaction mixture was stripped of solvent on a rotary evaporator leaving a pale yellow oil (2.76 g, 74% yield).

Example 2

DEM-BDDVE Oligomer: There were combined in a 2-neck 50 ml round bottom flask equipped with a nitrogen inlet, a magnetic stirrer and a reflux condenser 5.16 g (0.03 mol) diethyl maleate, 4.26 g (0.03 mol) 1,4-butanediol divinyl ether (BDDVE), 0.19 g (2 wt %) AIBN and 25 ml 1,2-dimethoxyethane. The reaction mixture was first flushed with nitrogen and then heated to 80° C. under a nitrogen atmosphere for 4 hours. After cooling, the reaction mixture was stripped of solvent on a rotary evaporator leaving the desired vinyl ether functional oligomer as a pale yellow oil (11 g, 100% yield).

Example 3

DEM-CMDVE Oligomer

There were combined in a 2-neck 50 ml round bottom flask equipped with a nitrogen inlet, a magnetic stirrer and a reflux condenser 5.16 g (0.03 mol) diethyl maleate, 5.88 g (0.03 mol) 1,4-cyclohexanedimethanol divinyl ether (CMDVE), 0.19 g (2 wt %) AIBN and 25 ml 1,2-dimethoxyethane. The reaction mixture was first flushed with nitrogen and then heated to 80° C. under a nitrogen atmosphere for 4 hours. After cooling, the reaction mixture was stripped of solvent on a rotary evaporator leaving a pale yellow oil (11.5 g, 100%). An infrared spectrum recorded on a Nicolet 4700

FT-IR spectrometer showed the presence of a prominent strong bands at 1616 cm$^{-1}$ and 1734.5 cm$^{-1}$ due respectively to the vinyl ether carbon-carbon double bonds and the carbonyl bond. At the same time, at 1404.8 cm$^{-1}$ assigned to the maleate double bond of DEM was absent.

Example 4

DBM-DVE-3 Oligomer: There were combined in a 2-neck 50 ml round bottom flask equipped with a nitrogen inlet, a magnetic stirrer and a reflux condenser 6.84 g (0.03 mol) dibutyl maleate, 6.06 g (0.03 mol) DVE-3, 0.25 g (2 wt %) AIBN and 25 ml 1,2-dimethoxyethane. The reaction mixture was first flushed with nitrogen and then heated to 80° C. under a nitrogen atmosphere for 5 hours. After cooling, the reaction mixture was stripped of solvent on a rotary evaporator leaving the desired vinyl ether functional oligomer as a pale yellow oil (13.9 g, 100% yield). Product is overweight due to incorporation of solvent.

Example 5

DEF-BDDVE Oligomer: There were combined in a 2-neck 50 ml round bottom flask equipped with a nitrogen inlet, a magnetic stirrer and a reflux condenser 5.16 g (0.03 mol) diethyl fumarate, 4.26 g (0.03 mol) 1,4-butanediol divinyl ether (BDDVE), 0.09 g (1 wt %) AIBN and 25 ml 1,2-dimethoxyethane. The reaction mixture was first flushed with nitrogen and then heated to 80° C. under a nitrogen atmosphere for 4 hours. After cooling, the reaction mixture was stripped of solvent on a rotary evaporator leaving the desired vinyl ether functional oligomer as a pale yellow oil (g, % yield).

Photopolymerization of Vinyl Ether Functional Reactive Oligomers.

Vinyl ether functional reactive oligomer; are exceptionally versatile with respect to their utility in photocurable applications. As shown in Scheme 1, they can be photopolymerized in three different modes.

Scheme 1: Photopolymerization reactions of vinyl ether functional reactive oligomers.

Mode #1. Cationic Photopolymerization

The most direct way in which vinyl ether functional reactive oligomers can be photopolymerized involves cationic polymerization. The addition of a cationic photoinitiator such as a diaryliodonium salt or a triarylsulfonium salt to the oligomer allows them to undergo polymerization on exposure to UV irradiation. An example is given in the sample temperature versus time plot shown in FIG. 1 determined by optical pyrometry (OP) in which an oligomer of diethyl maleate (DEM) and 1,4-butanediol divinyl ether (BDDVE) was combined with 2% by weight of (4-octyloxyphenyl)phenyliodonium hexafluoroantimonate (IOC-8 SbF$_6^-$). The trace shows that the photopolymerization starts slowly and then accelerates as irradiation proceeds.

Mode #2. Cationic Photopolymerization

To demonstrate this mode of photopolymerization, the above DEM-BDDVE reactive oligomer was combined with an equivalent weight of BDDVE and 2% by weight of IOC-8 SbF$_6^-$ based on the total weight of the mixture was added. The OP scan of the photopolymerization is shown in FIG. 2. The results show that after a short induction period, the photopolymerization is exceedingly rapid with the temperature rising to nearly 170° C. The induction period is likely due to the presence of KOH added as a stabilizer to the BDDVE by the manufacturer (BASF).

Mode #3. Radical Photopolymerization

Combining a vinyl ether functional oligomer with a maleate or fumarate monomer and a free radical photoinitiator allows a free radical alternating photocopolymerization to take place. An example is given in FIG. 3. In this experiment, an oligomer of DEM and BDDVE was combined with an equivalent of DEM and 2 wt % of 2-hydroxy-2,2-dimethylbenzophenone (Darocure-1173) Irradiation of the mixture as a thin film at 2700 mJ/cm$_2$ min in the optical pyrometer gave the curve shown. The mixture undergoes facile photopolymerization to provide a colorless, transparent, rigid film.

The polymerization with DMM is somewhat more rapid and exothermic than that with DEM. Both resulting polymers are rigid and transparent.

In FIG. 5 is shown the photopolymerization of the DEM-DVE-3 oligomer with 50% by weight of 1,6-hexanediol diacrylate. This polymerization is exceedingly fast and efficient. The copolymer film formed is quite hard and stiff. In the case of acrylate and methacrylate monomers that are added to the vinyl ether functional oligomers of this invention, amounts may be incorporated in amounts both equivalent to the molar amounts of vinyl ether groups present in the oligomer. Since these monomers also undergo free radical homopolymerization, they may also be added in amounts that exceed the molar amounts of the vinyl ether groups present in the oligomers.

While several aspects of the present invention have been described and depicted herein, alternative aspects may be effected by those skilled in the art to accomplish the same objectives. Accordingly, it is intended to cover all such alternative aspects as fall within the true spirit and scope of the invention.

I claim:

1. An oligomer comprising repeating units of formula I wherein

R$^1$ is a non-olefinic and non-acetylenic (C$_1$-C$_{10}$)hydrocarbon;

R$^2$ is a non-olefinic and non-acetylenic (C$_1$-C$_{10}$)hydrocarbon; and R$^3$ is a non-olefinic and non-acetylenic (C$_1$-C$_{24}$)hydrocarbon, wherein one or more alkylene (CH$_2$) optionally may be replaced by —O—, —S—, or SO$_2$ in each instance.

2. An oligomer according to claim 1 further comprising at least one unit of formula II 3. An oligomer obtainable by the process comprising reacting at least one monomer of formula A wherein R$^1$ is a non-olefinic and non-acetylenic (C$_1$-C$_{10}$)hydrocarbon;

R$^2$ is a non-olefinic and non-acetylenic (C$_1$-C$_{10}$)hydrocarbon;

with at least one monomer of formula B wherein R$^3$ is a non-olefinic and non-acetylenic (C$_1$-C$_{24}$) hydrocarbon group, wherein one or more alkylene (CH$_2$) optionally may be replaced by —O—, —S—, or SO$_2$ in each instance;

in the presence of a free radical initiator in a solvent with a chain transfer constant between 2000 and 20,000;

wherein the molar ratio of the monomer of formula A to the monomer of formula B is 1:1.

4. An oligomer according to claim 1, wherein R$^1$ and R$^2$ are both selected from methyl, ethyl, propyl, butyl, and 2-ethylhexyl.

5. An oligomer according to claim 1, wherein R$^3$ is selected from wherein X is selected from C(CH$_3$)$_2$, O, S, SO$_2$, CH$_2$ and a direct bond.

6. An oligomer according to claim 1, wherein R$^3$ is selected from (C$_1$-C$_8$)alkyl and (C$_1$-C$_8$)oxaalkyl.

7. An oligomer according to claim 3, wherein said free radical initiator is selected from an azo, hydroperoxy and peroxyalkyl initiator.

8. An oligomer according to claim 7, wherein said free radical initiator is 2,2'-Azobisisobutyronitrile.

9. An oligomer according to claim 3, wherein said solvent is selected from 1,2-dimethoxyethane, 1,4-dioxane, 1,3-dioxolane, tetrahydrofuran, diethylene glycol dimethyl ether and di(n-butyl) ether.

10. A process for preparing an oligomer comprising reacting a. a monomer of formula A wherein R$^1$ is a non-olefinic and non-acetylenic (C$_1$-C$_{10}$)hydrocarbon;

R$^2$ is a non-olefinic and non-acetylenic (C$_1$-C$_{10}$)hydrocarbon; and b. a monomer of formula B wherein R$^3$ is a non-olefinic and non-acetylenic (C$_1$-C$_{24}$) hydrocarbon, wherein one or more alkylene (CH$_2$) optionally may be replaced by —O—, —S—, or SO$_2$ in each instance;

in the presence of a free radical initiator in a solvent with a chain transfer constant between 2000 and 20,000;

wherein the molar ratio of the monomer of formula A to the monomer of formula B is 1:1.

11. A process according to claim 10, wherein R$^1$ and R$^2$ are both selected from methyl, ethyl, propyl, butyl, and 2-ethylhexyl.

12. A process according to claim 10, wherein R$^3$ is selected from wherein X is selected from C(CH$_3$)$_2$, O, S, SO$_2$, CH$_2$ and a direct bond.

13. A process according to claim 10, wherein R$^3$ is selected from (C$_1$-C$_8$)alkyl and (C$_1$-C$_8$)oxaalkyl.

14. A process according to claim 10, wherein said free radical initiator is selected from an azo, hydroperoxy and peroxyalkyl initiator.

15. A process according to claim 14, wherein said free radical initiator is 2,2'-Azobisisobutyronitrile.

16. A process according to claim 10, wherein said solvent is selected from 1,2-dimethoxyethane, 1,4-dioxane, 1,3-dioxolane, tetrahydrofuran, diethylene glycol dimethyl ether and di(n-butyl) ether.

17. A process for forming a polymer comprising:
   a. Combining at least one oligomer of claim 1 with a cationic photoinitiator; and
   b. Exposing the resulting combination to actinic irradiation.

18. A process according to claim 17 further comprising adding additional monomer of formula B to the oligomer and the cationic photoinitiator.

19. A process for forming a polymer comprising:
   a. Combining at least one oligomer of claim 1, at least one free radically polymerizable monomer and a free radical photoinitiator; and
   b. Exposing the resulting combination to actinic irradiation.

20. A process according to claim 19, wherein said free radically polymerizable monomer is a monomer of formula A added at a molar equivalent to the vinyl ether groups present in the oligomer.

\* \* \* \* \*